United States Patent
Popescu et al.

(10) Patent No.: US 7,519,208 B2
(45) Date of Patent: Apr. 14, 2009

(54) METHOD AND APPARATUS FOR ERROR-TOLERANT DATA TRANSFER FOR A CT SYSTEM

(75) Inventors: Stefan Popescu, Erlangen (DE); Martin Bauer, Bräuningshof (DE); Wolfgang Edler, Erlangen (DE); Gerd Neubauer, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 712 days.

(21) Appl. No.: 11/112,534

(22) Filed: Apr. 22, 2005

(65) Prior Publication Data

US 2005/0249326 A1    Nov. 10, 2005

(30) Foreign Application Priority Data

Apr. 22, 2004    (DE)    ........................ 10 2004 019 598

(51) Int. Cl.
*G06K 9/00* (2006.01)

(52) U.S. Cl. .................................... 382/128; 382/131
(58) Field of Classification Search ................. 382/128, 382/131
See application file for complete search history.

(56) References Cited

U.S. PATENT DOCUMENTS

| 6,914,957 | B2 * | 7/2005 | Dafni et al. ................... 378/15 |
| 7,050,616 | B2 * | 5/2006 | Hsieh et al. ................. 382/131 |
| 2002/0174403 | A1 | 11/2002 | Chethik |
| 2003/0185427 | A1 | 10/2003 | Hsieh et al. |
| 2003/0229840 | A1 | 12/2003 | Pattavina |

FOREIGN PATENT DOCUMENTS

| JP | 63045762 | 9/1989 |
| WO | WO 01/28252 | 4/2001 |

* cited by examiner

*Primary Examiner*—Tom Y Lu
(74) *Attorney, Agent, or Firm*—Schiff Hardin LLP

(57) ABSTRACT

In a CT system and a method for error-tolerant data transfer between a data acquisition unit and an image reconstruction unit therein, digital data are divided into data packets and are transferred as a data stream from a transmission device to a reception device and are buffered in the reception device for further processing. The data packets are selected such that they respectively contain the data of a segment of a detector row or of a complete detector row of the CT system. Incomplete and/or missing focal paths are detected in the reception device and a storage region is reserved and marked as incorrect for these data packets. The incorrect and/or missing data packets are later interpolated from the data of adjacent detector rows and/or adjacent segments of a detector row and/or successive projections precede or follow the incorrect and/or missing data packets. Missing data packets due to transfer interferences can also be tolerated.

16 Claims, 2 Drawing Sheets

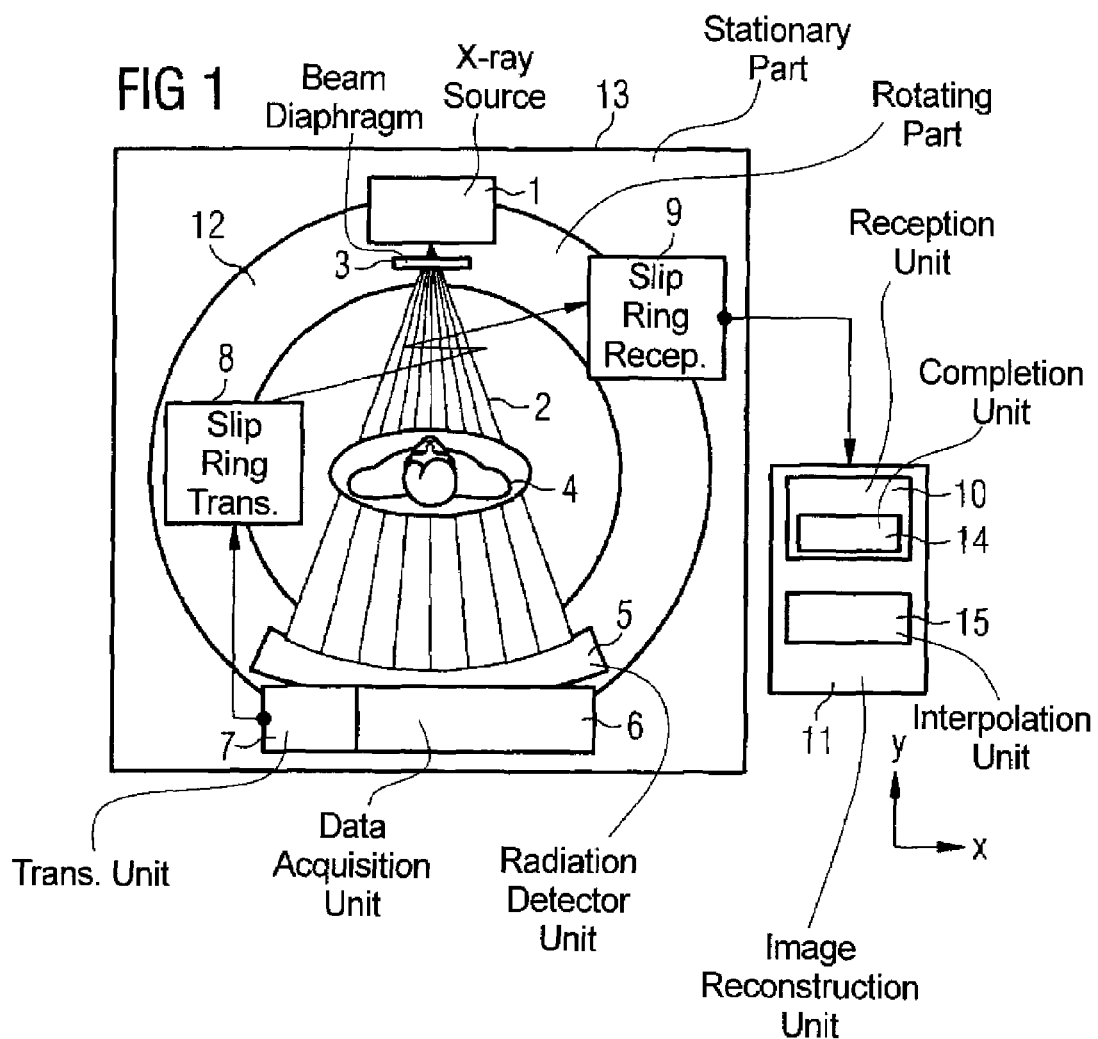

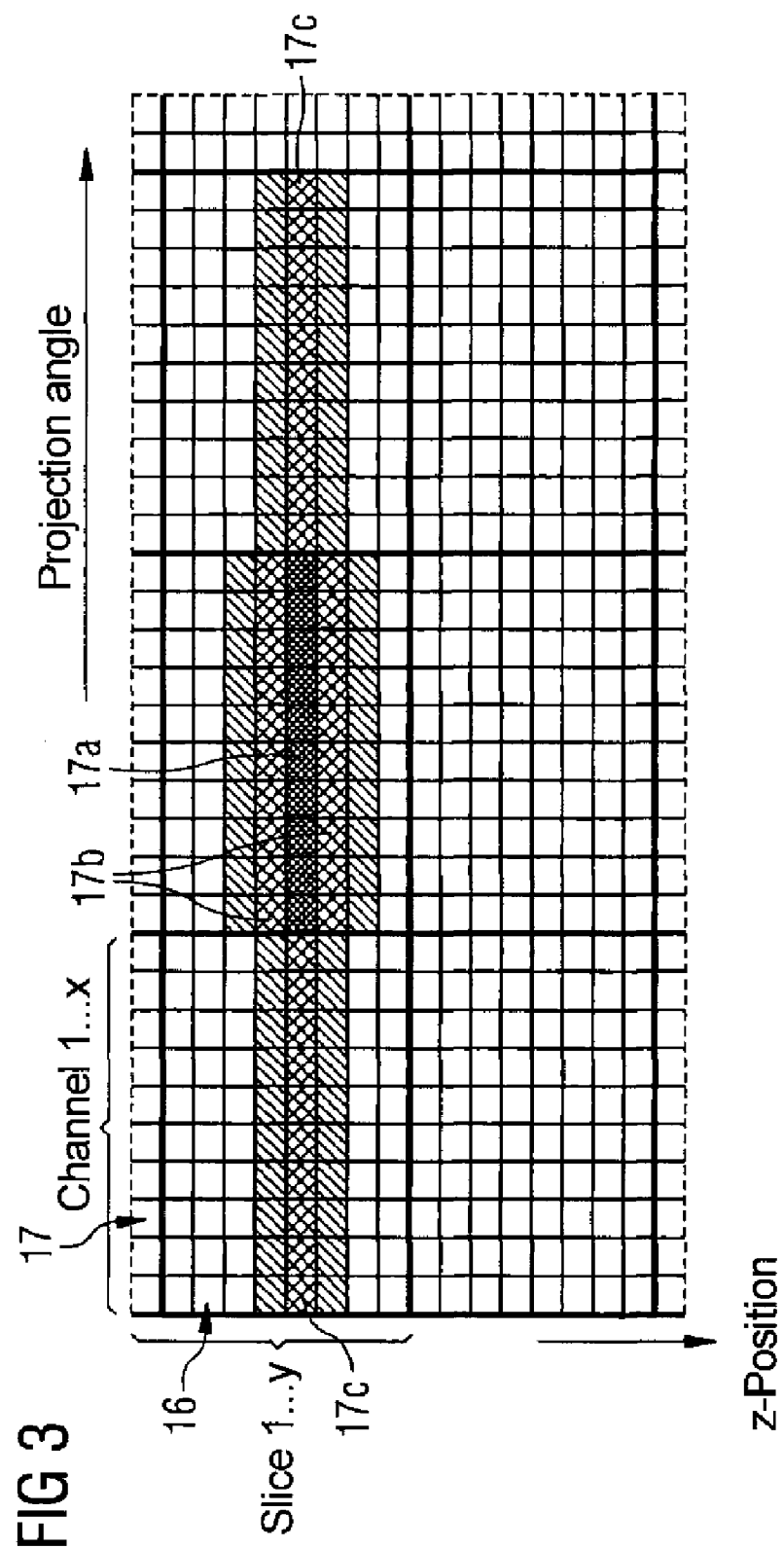

METHOD AND APPARATUS FOR ERROR-TOLERANT DATA TRANSFER FOR A CT SYSTEM

BACKGROUND OF THE INVENTION

1. Field of the Invention

The present invention concerns a method for error-tolerant data transfer between a data acquisition unit and an image reconstruction device of a CT system of the type wherein digital data are divided into data packets and are transferred as a data stream from a transmission device to a reception device and are buffered (cached) in the reception device for further processing. The invention also concerns a computed tomography (CT) system with such an apparatus for data transfer between a data acquisition unit and an image reconstruction device.

2. Description of the Prior Art

Error-free data transfer is important in many technical fields. In the field of imaging, particularly medical imaging, optimal error-free transfer of the measurement data from the data acquisition unit at the measurement location to the image reconstruction unit is an important requirement for achieving a high-quality image reconstruction. The problem of transfer errors in particular occurs with wireless transfer techniques as used, for example, in computed tomography systems. Data transfer ensues in CT systems via an optical or capacitive slip ring between the rotating part and the stationary part in order to be able to transfer measurement data acquired by the data acquisition unit at the measurement location to the stationary image reconstruction device during the measurement. This data transfer technique in CT systems, however, is sensitive to external interferences that can cause incorrect data bits in the data transfer. While these bit errors frequently can be corrected using suitable error correction techniques, but an interruption of the data transfer or an occasional missing synchronization between the transmission device and the reception device lead to larger problems. Such interruptions occur with higher probability in multi-slice CT systems because external interferences influence a larger number of data bits due to the very high transfer rate in these systems within the same time duration as in other systems. In current multi-slice CT systems, the measurement data are transferred in a serial bit stream in which the serial bit clock is embedded. The reception device extracts the embedded clock in order to decode the bit stream. Furthermore, special serial codes are periodically transferred with the bit stream in order to achieve a byte and packet synchronization. An external interference can lead to an error in the transfer of these synchronization codes that can result in a desynchronization. In this case, transferred data packets are not received or decoded or are only incompletely received or decoded, such that they are missing for the subsequent image reconstruction.

Due to missing data packets in the transmission of the measurement data in a computed tomography system, it may be necessary to interrupt the entire measurement process because a correct image reconstruction is no longer possible due to the missing data. This has as a consequence a loss of expensive contrast agent (if used in the examination), an increased patent radiation exposure and additional time expenditure.

A method for error-tolerant data transfer is known from U.S. Pat. Application Publication No. 2003/0185427, in which incorrect data bits in the transferred data packets are replaced by bit values that are interpolated from adjacent data packets. The incorrect data packets can be identified by an error checksum transferred with the data packets.

Furthermore, in a technique known as FEC (Forward Error Correction), additional coding bits, from which the correct values of incorrect data bits can be reconstructed, are transferred together with the data.

U.S. Pat. Application Publication No. 2003/0229840 concerns a method for forward correction (FEC) in the transfer of data packets over a network. In this method, additional parity packets, from which later missing data packets can be recovered, are generated from the data packets to be transferred. These parity packets must be transferred over the network in addition to the data packets and thus reduce the data transfer rate. Use of this technique in CT systems therefore is not advantageous. Missing data packets normally are recovered from the information in the parity packets. Given unrecoverable packets, it is proposed either to replace these with predetermined replacement packets or to form an average value from the data of a number of preceding and subsequent data packets, and to replace the missing data packet with an average data packet so obtained. These method steps ensue in the JPEC decoder of the reception device discussed in that published application.

U.S. Pat. Application Publication No. 2002/174403 also concerns a method for data transfer in a network in which additional parity packets are generated and transferred. The transfer ensues in a multidimensional matrix that is intended to make the later recovery of lost data packets via the parity packets easier. Missing data packets are represented with a placeholder upon receipt of the matrix and are subsequently reconstructed using the parity packets. Missing data packets, for which a recovery via the parity packets is not possible, are not replaced.

PCT Application WO 01/28252 discloses a method for image coding in which the data transfer ensues with redundant block code and auxiliary data that are progressively coded for each image. It is thus a method for transfer of images, rather than measurement data or raw data from which corresponding image data then can be generated in the image processing unit of a CT system downstream from the reception device.

The abstract of Japanese Application 01221958 discloses an interpolation circuit for an incorrect data packet. In this circuit, two separate reception buffers are provided, of which one serves for acquisition of normal data packets and the other serves for acquisition of defective data packets or data packets to be interpolated.

SUMMARY OF THE INVENTION

An object of the present invention is to provide a method as well as an apparatus for a CT system for error-tolerant data transfer with which a larger number of missing data packets can be tolerated in the data transfer or upon decoding of the received data.

The object is achieved by a method for error-tolerant data transfer, wherein digital data are divided into data packets and are transferred as a data stream from a transmission device to a reception device and are buffered in the reception device for a further processing and wherein missing data in data packets and/or missing data packets are detected in the reception device and a storage region is reserved and marked as "incorrect" for these missing data or data packets. At a later point in time, the incomplete and/or missing data packets are then interpolated from data packets preceding or subsequent to the data. A significant feature of this method is thus that a storage region is reserved for the missing data or data packets as if this storage region contained received data packets that contain only incorrect data. This can also ensue by describing the respective storage region with arbitrary values. In the case of missing bits in individual data packets, these bits of the data packet preferably are filled with arbitrary bit values and the data packet completed in this manner is marked as incorrect. Since a missing packet obviously cannot be stored in the case of a missing data packet, a location in the storage region corresponding to the detected missing packet is marked as occupied with an incorrect data packet. The data packets marked as incorrect are then interpolated at a later point in time (after the further data packets have been transferred) from the data packets transferred preceding and/or subsequent to the data packets marked as incorrect.

The measurement data are divided into the data packets such that each data packet contains the measurement data of a contiguous segment of a detector row or the measurement data of the entire detector row of the CT radiation detector unit. In this manner, a two-dimensional matrix can be created in the reception direction with the received data packets that is reproduced from the rows and, if applicable, the row segments, of the detector unit of the computer tomography apparatus. This matrix is expanded in the row direction by attachment of the different projections under which the measurement data have respectively been acquired. In this manner, a missing data packet can be interpolated both from the data packets of adjacent rows and from the data packets of the same row of the adjacent projections.

The size of the data packets provided by the transmission device preferably is selected dependent on the typically-occurring interferences, such that not too many data packets in direct succession are lost due to these interferences and a later interpolation is enabled. Given the transfer of data that represent a multi-dimensional connection, such as, for example, two-dimensional slice image data or three-dimensional volume data, before the transfer the acquired measurement data preferably are combined into a corresponding multi-dimensional matrix of data packets that is appropriate for the type of examination.

The data packets preferably are provided with a marker that unambiguously identifies their position within the data stream before their transfer. This marker, for example, can be a consecutive numbering of the transferred data packets that serves as an address of the respective data packet within the data stream. By monitoring these markers of the incoming or decoded data packets at the receiver, missing data packets can be reliably detected at any time. Missing data within a data packet are recognized without anything further due to the length of the respective data packet being too short.

Furthermore, as before it is advantageous to provide the data packets with a check code, for example a checksum, in order to be able to detect and later correct in the reception device not only missing data but also individual bit errors within a data packet.

In a further embodiment of the present method as well as of the associated apparatus, the number and distribution of the data packets detected as missing, incorrect or incomplete are monitored in real time. Upon exceeding predeterminable limit values that indicate a further processing of the data in a reasonable manner is no longer enabled, the data transfer or the measurement forming the basis of this data transfer is then interrupted. The magnitude of these limit values depends on the respective application.

The apparatus in the form of a CT system for implementation of the present method has a transmission device for transfer of the digital data in data packets to a reception device that has a storage unit (in particular a reception buffer or cache) for buffering the data packets, and the reception device also has a completion module that detects missing data in data packets and/or missing data packets and reserves and marks as "incorrect" a storage region for the missing data or data packets. The transmission device is fashioned such that it transfers data of a segment of a detector row or of a complete detector row of the CT system as one data packet. Furthermore, an interpolation module is provided as a component of the apparatus. This interpolation module later interpolates the missing and/or incomplete data packets, as well as data packets detected as incorrect from the data (that are contained in preceding or subsequent data packets), using data from adjacent detector rows and/or adjacent segments of a detector row and/or successive projections.

The interpolation module preferably is a component of the image reconstruction unit. The completion module, for example, can be fashioned as a programmable logic unit, in particular as an FPGA (Field Programmable Gate Array).

In principle, the interpolation can ensue with known methods as are described in the previously-cited U.S. Pat. Application Publication No. 2003/1085427, the teachings of which are incorporated herein by reference. In particular the interpolation of the data packets or data marked as incorrect can ensue in the same manner as in the method described in this document since, with the inventive method, the storage content is provided to the interpolation module as if no missing data packets or data were present, but rather only incorrect data.

DESCRIPTION OF THE DRAWINGS

FIG. 1 schematically illustrates an exemplary embodiment for a data transfer apparatus in a computed tomography apparatus in accordance with the invention.

FIG. 2 is a table for explaining an incorrect data transfer.

FIG. 3 is an example for a two-dimensional organization of the data packets as well as possibilities for interpolation in accordance with the invention.

DESCRIPTION OF THE PREFERRED EMBODIMENTS

FIG. 1 shows an embodiment of a device for data transfer according to the present invention in a volume CT system. An x-ray tube 1 attached on a rotatable part 12, known as the gantry, generates a conical x-ray 2, the aperture angle of which can be set in the x-direction and z-direction by the mechanically adjustable collimator 3. FIG. 1 shows a section perpendicular to the z-direction. The x-ray beam 2 penetrates a patient body 4 and strikes a planar detector unit 5. In a multi-slice CT system as in the present example, this detector unit 5 has a two-dimensional matrix of detector elements with a number of detector rows and detector columns. Each detector row provides measurement data for the reconstruction of a slice of the patient body and has a number of detector channels or detector elements. A data acquisition unit 6 on the rotatable part 12 converts the analog measurement signals acquired by the detector elements of the detector unit 5 and supplies a serial stream of digital measurement data. In the transmission unit 7, these digital measurement data are combined into individual data packets and are transferred via the transmitted 8 to the receiver 9 at the stationary part 13 of the CT system. The transmitter 8 and the receiver 9 are fashioned as a slip ring transfer device as is known in the art. The transferred data packets are supplied to the reception unit 10, which is fashioned as part of the image reconstruction device 11 in the present case. The received bit stream is decoded in the reception unit 10. The images of the individual slices of the examination region of the patient 4 acquired with the acquisition system composed of the x-ray tube 1 and the detector unit 5 are reconstructed from the retrieved measurement data.

In the present example, the reception unit 10 also includes the completion module 14 and the image reconstruction unit 11 includes the interpolation module 15, which is discussed in detail below.

The data acquired by the data acquisition unit 6 are divided in the transmission unit 7 into smaller data packets. The size of the data packets is selected such that missing data packets can be interpolated using data packets transmitted before or afterwards. In the present example, each data packet contains the data of a complete detector row, i.e. all channels or all detector elements of this detector row. A consecutive packet number is associated with each individual data packet, such that a missing packet number can be identified. Furthermore each data packet contains a check code with which bit errors in the transfer of the data packet can be detected.

The rotatable part 12 of the computed tomography system rotates continuously around the z-axis during a scan. During this rotation, the acquired data are continuously transferred to the reception unit 10 in real time. If interferences occur in this transfer, the data packets received by the reception unit 10 can contain incorrect bits or whole data packets can be lost. FIG. 2 shows an example for such an incorrect transfer in the form of a table in which the left column shows the consecutive numbering of the individually transferred data packets, the second column shows the correct or incorrect check code, the third column shows the type of the transfer interference, the fourth column sows the data packets stored in the storage of the reception unit according to the present method and the right column shows the status of the respective data packet with which this packet is marked in the storage. From the table it can be seen that in this example the data packet with the packet number N+2 was incomplete or was received with a false checksum. This data packet is nevertheless stored as a complete data packet and marked as incorrect. After receipt of the data packet with the packet number N+3 with the correct check code, the reception unit recognizes, as the next data packet, the data packet with the packet number N+6 that is likewise received with the correct check code. The reception unit therefore establishes two missing data packets, but reserves storage space in the reception buffer for both missing packets N+4 and N+5, and marks these as incorrect.

After receipt of all measurement data to be transferred, the data packets marked as incorrect are interpolated from the data of data packets transferred beforehand or afterwards. This can ensue by means of linear interpolation, quadratic interpolation or interpolation of a higher order. The interpolation ensues for all data packets marked as incorrect, independent of whether they are originally missing data packets or correctly received data packets with individual bit errors.

The content of the respective data packets marked as incorrect thus is replaced by the interpolated values. This is simplified in the present example by the structuring of the data in the transmission, since the received data packets can be arranged as a two-dimensional matrix that reproduces the geometry of the detector unit of the CT system, the successive projections and the shifting of the patient table in the z-direction. This can be seen in FIG. 3, which reproduces the significant framing of the detector rows 16 and detector columns channels 17 of the detector unit 5. The projections following in succession (which were acquired in the measurement) attach to the right, the shifting of the patient table in the z-direction attaches below.

Given a projection, if an error is determined in a data packet that (in the present example) contains the data of all channels of a detector row 17a or this is marked as incorrect, the data of this data packet can be interpolated using the data of adjacent data packets. In the present example, this concerns the data of the data packets of the adjacent detector rows 17b that were transmitted immediately before and after this data packet 17a as well as the data of the data packets 17c that were acquired by the same detector row at a projection angle lying immediately before and after this data packet. By the division of the data into the data packets shown in the present example, a simple interpolation thus can be implemented based on the geometric context. In the present example, the reception unit 10 can also implement a real-time monitoring and analysis of the total number of missing or incorrect data packets by means of software or a programmable logic unit in order to interrupt the data transfer and the measurement given a predeterminable limit value being exceeded within specific time spans or data quantities. The limit value in the present example is selected such that, as long as it is not exceeded, an image reconstruction without image artifacts is still possible from the transmitted and interpolated data.

Although modifications and changes may be suggested by those skilled in the art, it is the intention of the inventors to embody within the patent warranted hereon all changes and modifications as reasonably and properly come within the scope of their contribution to the art.

We claim as our invention:

1. In a computed tomography system having a radiation detector with a plurality of detector rows, said radiation detector supplying output signals, resulting from irradiation of a subject in the computed tomography system, to a data acquisition unit and said data acquisition unit generating digital data from the respective output signals, a method for error-tolerant data transfer between the data acquisition and an image reconstruction unit remote therefrom comprising the steps of:

in said data acquisition unit, dividing said digital data into data packets each comprising multiple bits and transferring said data packets, as a data stream, from a transmission device, in communication with the data acquisition unit, to a reception device, in communication with the image reconstruction unit, and buffering said data packets in said reception device;

in said data acquisition unit, formulating said data packets so that each packet comprises only data bits selected from the group consisting of data bits of a segment on one detector row and data bits of one complete detector row;

in said reception device, detecting incomplete and/or missing data packets in said data stream;

for each data packet detected as incomplete, storing the incomplete data packet in a storage region at the reception device and marking that storage region as a marked storage region;

for each data packet detected as missing, marking a storage region at the reception device therefor, as a marked storage region; and for each of said marked storage regions, interpolating data in said reception device to complete an incomplete data packet or to replace a missing data packet, from data selected from the group consisting of data from adjacent segments of the same detector row if said data packets comprise said data bits of a segment of one detector row, and data from an adjacent detector row if said data packets comprise said data bits of one complete detector row.

2. A method as claimed in claim 1 comprising irradiating the subject in said computed tomography system in a plurality of successive projections and generating said output signals from said detector unit and said data packets in said data acquisition unit for each of said projections, and selecting said data in said group for interpolating said incomplete and/or missing data packet from adjacent segments in said one detector row in a next-successive projection or from adjacent detector rows to said one complete detector row in a next-successive projection.

3. A method as claimed in claim 1 comprising also detecting complete but incorrect data packets in said reception device, storing each complete but incorrect data packet in a data region at said storage device and marking that data region as a marked data region, and interpolating each complete but incorrect data packet in each marked region together with interpolation of said incorrect and/or missing data packets in said respective marked regions.

4. A method as claimed in claim 1 wherein said radiation detector is a multi-dimensional radiation detector that generates said output signals representing multi-dimensional data, and comprising, in said data acquisition unit, formulating said data packets by dividing said data packets into a multi-dimensional matrix conforming to said multi-dimensional output signals.

5. A method as claimed in claim 1 comprising, before transferring said data packets from said transmission device to said reception device, marking each data packet with a marker that uniquejy identifies a position of that data packet in said data stream.

6. A method as claimed in claim 1 comprising, before transferring said data packets in said data stream from said transmission device to said reception device, formulating a check code for each data packet, and transferring the respective check codes with the data packets, and detecting said incorrect and/or missing data packets using said check code.

7. A method as claimed in claim 1 comprising monitoring a number of said incorrect and/or missing data packets in real time during transfer of said data packets in said data stream from said transmission device to said reception device, and interrupting transfer of said data packets in said data stream from said transmission device to said reception device if said number exceeds a predetermined limit value.

8. A method as claimed in claim 1 comprising monitoring a distribution of said incorrect and/or missing data packets in real time during transfer of said data packets in said data stream from said transmission device to said reception device, and interrupting transfer of said data packets in said data stream from said transmission device to said reception device if said distribution exceeds a predetermined limit value.

9. A computed tomography system comprising:
a radiation detector with a plurality of detector rows, said radiation detector generating output signals resulting from irradiation of a subject;
a data acquisition unit that generates digital data bits from the respective output signals and divides said digital data bits into data packets, each comprising multiple bits, forming a data stream, said data acquisition unit formulating said data packets so that each packet comprises only data bits selected from the group consisting of data bits of a segment on one detector row and data bits of one complete detector row;
a transmission device in communication with the data acquisition unit and supplied with said data stream therefrom;
an image reconstruction unit; and
a reception device, in communication with the image reconstruction unit, in which said data packets are buffered before being supplied to said image reconstruction unit, said reception device detecting incomplete and/or missing data packets in said data stream and for each data packet detected as incomplete, storing the incomplete data packet in a storage region at the reception device and marking that storage region as a marked storage region, and for each data packet detected as missing, marking a storage region at the reception device therefor as a marked storage region, and said reception device, for each of said marked storage regions, interpolating data to complete an incomplete data packet or to replace a missing data packet, from data selected from the group consisting of data from adjacent segments of the same detector row if said data packets comprise said data bits of a segment of one detector row, and data from an adjacent detector row if said data packets comprise said data bits of one complete detector row.

10. A computed tomography system as claimed in claim 9 comprising an x-ray source that irradiates the subject in a plurality of successive projections and wherein said detector unit generates said output signals, and said data acquisition unit generates said data packets, for each of said projections, and wherein said reception device selects said data in said group for interpolating said incomplete and/or missing data packet from adjacent segments in said one detector row in a next-successive projection or from adjacent detector rows to said one complete detector row in a next-successive projection.

11. A computed tomography system as claimed in claim 9 wherein said reception unit also detects complete but incorrect data packets and stores each complete but incorrect data packet in a data region at said storage device and marks that data region as a marked data region, and interpolates each complete but incorrect data packet in each marked region together with interpolation of said incorrect and/or missing data packets in said respective marked regions.

12. A computed tomography system as claimed in claim 9 wherein said radiation detector is a multi-dimensional radiation detector that generates said output signals representing multi-dimensional data, and wherein said data acquisition unit formulates said data packets by dividing said data packets into a multi-dimensional matrix conforming to said multi-dimensional output signals.

13. A computed tomography system as claimed in claim 9 wherein said data acquisition unit marks each data packet with a marker that uniquely identifies a position of that data packet in said data stream.

14. A computed tomography system as claimed in claim 9 wherein said data acquisition unit formulates a check code for each data packet, and wherein the transmission device transmits the respective check codes with the data packets to said reception device, and wherein said reception device detects said incorrect and/or missing data packets using said check code.

15. A computed tomography system as claimed in claim 9 wherein said reception device monitors a number of said incorrect and/or missing data packets in real time during transmission of said data packets in said data stream from said transmission device to said reception device, and interrupts transfer of said data packets in said data stream from said transmission device to said reception device if said number exceeds a predetermined limit value.

16. A computed tomography system as claimed in claim 9 wherein said reception device monitors a distribution of said incorrect and/or missing data packets in real time during transmission of said data packets in said data stream from said transmission device to said reception device, and interrupts transfer of said data packets in said data stream from said transmission device to said reception device if said distribution exceeds a predetermined limit value.

* * * * *